(12) United States Patent
Toth et al.

(10) Patent No.: US 8,086,012 B2
(45) Date of Patent: Dec. 27, 2011

(54) METHODS AND APPARATUS FOR DETERMINING BODY WEIGHT AND FAT CONTENT USING COMPUTED TOMOGRAPHY DATA

(75) Inventors: Thomas Louis Toth, Brookfield, WI (US); Daniele Marin, Durham, NC (US); Lisa Ho, Durham, NC (US); Rendon Nelson, Durham, NC (US)

(73) Assignee: General Electric Company, Schenectady, NY (US)

( * ) Notice: Subject to any disclaimer, the term of this patent is extended or adjusted under 35 U.S.C. 154(b) by 716 days.

(21) Appl. No.: 12/253,889

(22) Filed: Oct. 17, 2008

(65) Prior Publication Data

US 2010/0098310 A1 Apr. 22, 2010

(51) Int. Cl.
*G06K 9/00* (2006.01)
*G01N 23/00* (2006.01)
*G01B 15/02* (2006.01)
(52) U.S. Cl. ............... 382/131; 378/4; 378/54
(58) Field of Classification Search .......... 378/4, 19, 378/37, 50, 54, 89; 382/128, 130–132
See application file for complete search history.

(56) References Cited

U.S. PATENT DOCUMENTS

| 6,999,549 B2* | 2/2006 | Sabol et al. ............... 378/5 |
| 7,203,274 B2* | 4/2007 | Charles et al. ............ 378/54 |
| 2004/0101086 A1* | 5/2004 | Sabol et al. ............... 378/4 |
| 2004/0101184 A1* | 5/2004 | Sivaramakrishna et al. .. 382/131 |
| 2008/0123920 A1 | 5/2008 | Toth et al. |

OTHER PUBLICATIONS

Thomas Toth, Zhanyu Ge and Michael P. Daly, The Influence of Patient Centering on CT Dose and Image Noise, Med. Phys. 34 (7), Jul. 2007, pp. 3093-3101.

* cited by examiner

*Primary Examiner* — Irakli Kiknadze
(74) *Attorney, Agent, or Firm* — Dean D. Small; The Small Patent Law Group

(57) ABSTRACT

Methods and apparatus for determining body weight and fat content using computed tomography data are provided. One method includes acquiring a pre-scan image using a computed tomography imaging system and segmenting the pre-scan image into pixels representing imaged fat and pixels representing imaged tissue. The method further includes determining a lean body weight based on the segmented pixels representing imaged fat and imaged tissue.

23 Claims, 5 Drawing Sheets

US 8,086,012 B2

METHODS AND APPARATUS FOR DETERMINING BODY WEIGHT AND FAT CONTENT USING COMPUTED TOMOGRAPHY DATA

BACKGROUND OF THE INVENTION

This invention relates generally to imaging methods and apparatus, and more particularly to methods and apparatus using computed tomography (CT) data.

Characteristics of an individual, such as body weight, height, girth, gender, age, etc. are clinical descriptors useful by physicians to predict certain risks, for example, mortality and morbidity risk. Metrics such as Body Mass Index (BMI) and Lean Body Weight (LBW) that account for body fat composition may provide even better information to predict the risk of mortality and morbidity for a particular individual, as well as provide a more accurate parameter for an appropriate tailoring of pharmacologic interventions.

BMI is a measure of body fat based on height and weight that applies to both men and women. LBW is a person's total body weight minus the weight of adipose tissue (fat). LBW is generally estimated using a body composition weight analyzer scale that measures leg-to-leg bioelectrical impedance. However, these estimates can be affected by several compounding factors, such as an individual's hydration status or the amount of fluid in the urinary bladder and small bowel loops. The greater the error in the estimate, the greater the likelihood that, for example, the dose and rate of an administered contrast medium is not correct or optimal for a patient. Thus, imaging quality may be adversely affected, for example, when performing a CT image scan of a person injected with a contrast medium. Moreover, administering too much contrast agent can result in increased risk and severity of contrast-induced allergic reactions. Additionally, routine assessments of leg-to-leg impedance may not be practical in standard clinical practice.

BRIEF DESCRIPTION OF THE INVENTION

In one aspect, some embodiments of the present invention provide a method for determining lean body weight. The method includes acquiring a pre-scan image using a computed tomography imaging system and segmenting the pre-scan image into pixels representing imaged fat and pixels representing imaged tissue. The method further includes determining a lean body weight based on the segmented pixels representing imaged fat and imaged tissue.

In another aspect, some embodiments of the present invention provide a method for determining lean body weight of a person using a computed tomography (CT) scan. The method includes performing a scout scan of an abdomen of the person to acquire an image and thresholding the image to identify pixels representing imaged fat and pixels representing imaged tissue. The method further includes calculating a fat ratio based on the identified pixels representing imaged fat and imaged tissue and determining a lean body weight for the person based on the fat ratio and a weight of the person.

In yet another aspect, some embodiments of the present invention provide a computed tomography system that includes an imaging portion configured to acquire a scout scan of a person. The computed tomography system further includes a processing portion configured to threshold an image generated from the scout scan to identify pixels representing imaged fat and pixels representing imaged tissue, and to calculate a lean body weight of the person based on a fat ratio determined from the identified pixels.

DETAILED DESCRIPTION OF THE INVENTION

Figure 1:
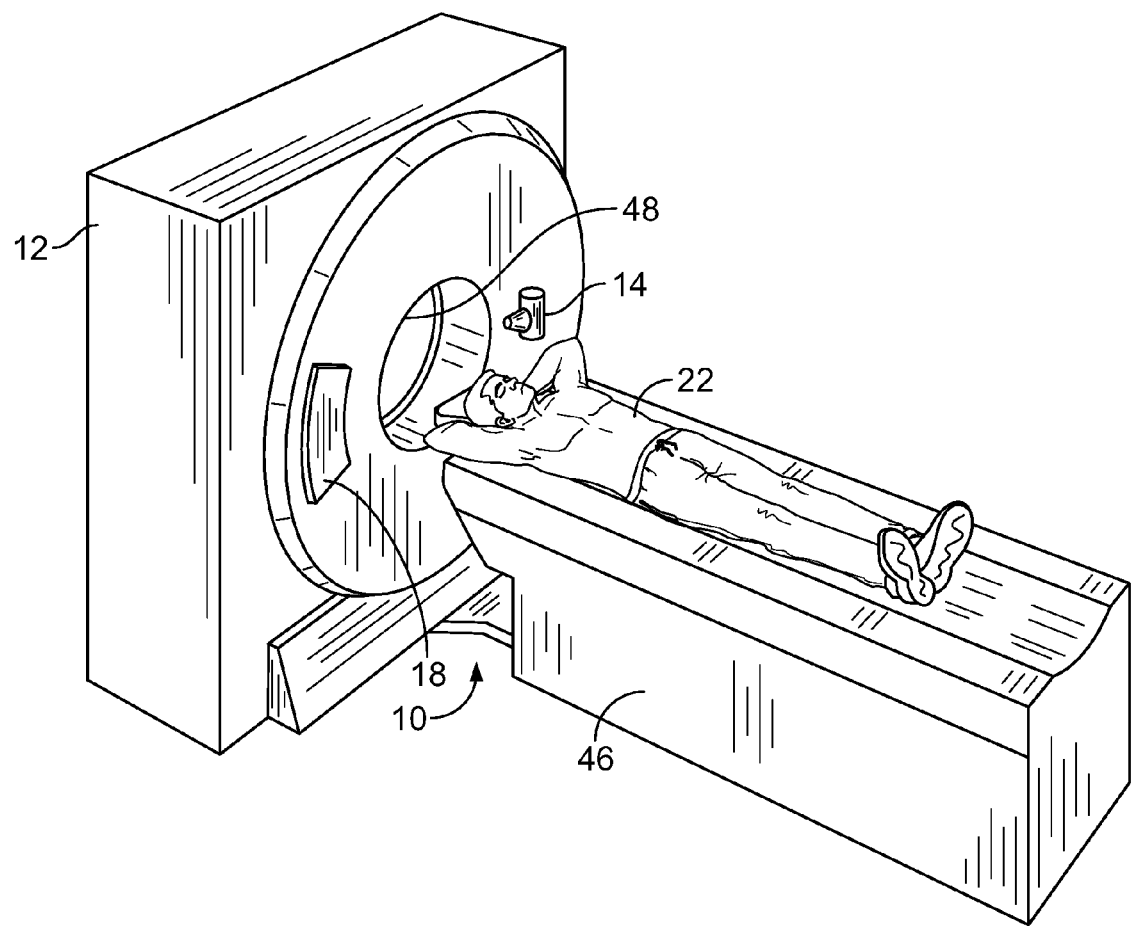
FIG. 1 is a perspective view of a computed tomography (CT) imaging system constructed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings, nor are the figures necessarily drawn to scale.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Additionally, the recitation of a particular number of elements does not exclude embodiments having more than that particular number, unless the number is further qualified by words such as "exactly" or "only." Also, unless the possibility is either explicitly, logically, or physically excluded, individual features may be omitted from an embodiment, or one or more features from another embodiment or other embodiments, may be combined to produce additional embodiments of the present invention.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Various embodiments may be implemented in connection with different types of imaging systems. For example, various embodiments may be implemented in connection with a CT imaging system in which an x-ray source projects a fan-shaped beam that is collimated to lie within an X-Y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, a patient or object (e.g., baggage) is moved while the data for a prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighting algorithms that weight the acquired data as a function of view angle and detector channel index. Specifically, prior to a filtered backprojection process, the data is weighted according to a helical weighing factor, which is a function of both the gantry angle and the detector angle. The weighted data is then processed to generate CT numbers and to construct an image that corresponds to a two-dimensional slice taken through the object.

Technical effects of embodiments of the present invention include improved and more consistent diagnostic image quality produced when estimating Lean Body Weight (LBW) using CT data. Moreover, contrast medium administration can be optimized based on the estimated LBW. The manner in which these and other technical effects of embodiments of the present invention are achieved will become apparent to one of ordinary skill in the art upon based on the subject matter described herein.

Figure 2:
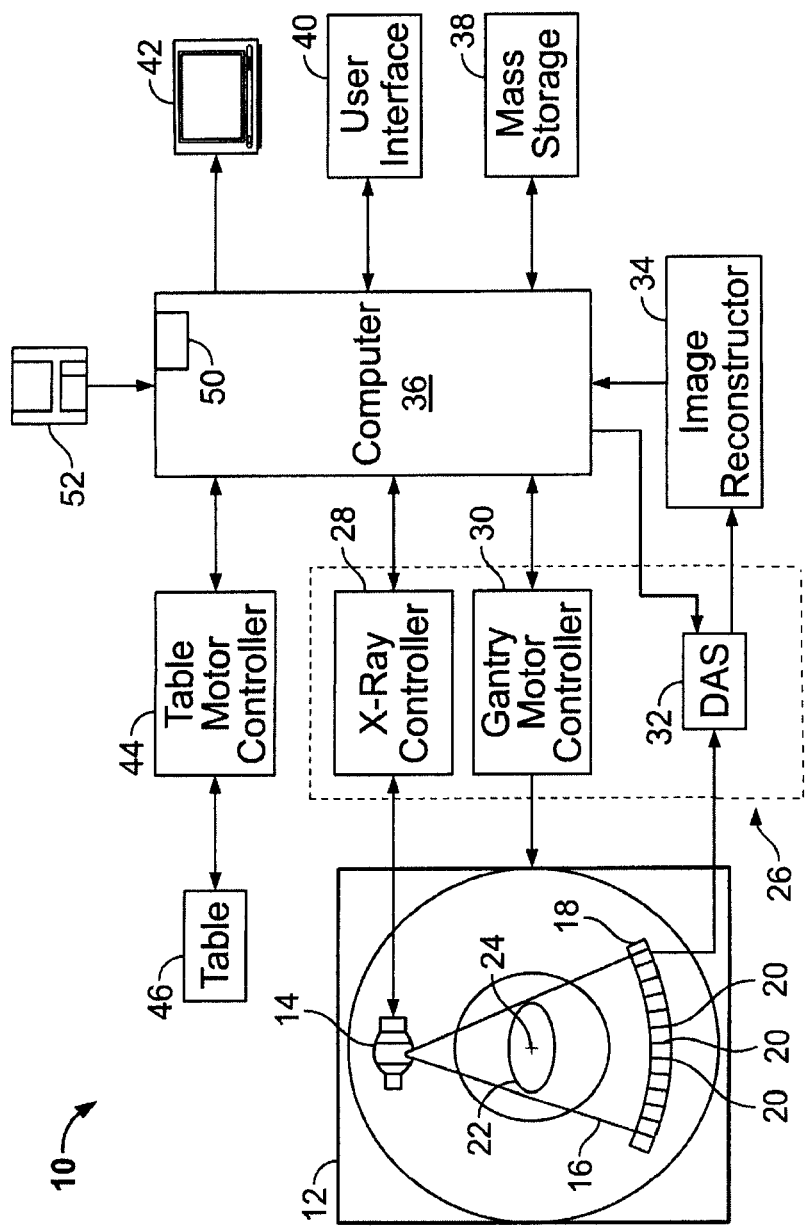
FIG. 2 is a block diagram of a CT imaging system constructed in accordance with various embodiments of the invention.

FIG. 1 is a pictorial view of a CT imaging system 10. FIG. 2 is a block schematic diagram of the CT imaging system 10 illustrated in FIG. 1. In the exemplary embodiment, a computed tomography (CT) imaging system 10 is shown as including a gantry 12 representative of a "third generation" CT imaging system. The gantry 12 has a radiation source 14 that projects a cone beam 16 of X-rays toward a detector array 18 on the opposite side of the gantry 12.

The detector array 18 is formed by a plurality of detector rows (not shown) including a plurality of detector elements 20 that together sense the projected X-ray beams that pass through an object, such as a medical patient 22. Each detector element 20 produces an electrical signal that represents the intensity of an impinging radiation beam and hence the attenuation of the beam as it passes through object or patient 22. The CT imaging system 10 having a multislice detector array 18 is capable of providing a plurality of images representative of a volume of patient 22. Each image of the plurality of images corresponds to a separate "slice" of the volume. The "thickness" or aperture of the slice is dependent upon the thickness of the detector rows.

During a scan to acquire radiation projection data, the gantry 12 and the components mounted thereon rotate about a center of rotation 24. FIG. 2 shows only a single row of detector elements 20 (i.e., a detector row). However, the multislice detector array 18 includes a plurality of parallel detector rows of detector elements 20 such that projection data corresponding to a plurality of quasi-parallel or parallel slices can be acquired simultaneously during a scan.

Rotation of the gantry 12 and the operation of the radiation source 14 are governed by a control mechanism 26 of the CT imaging system 10. The control mechanism 26 includes a radiation controller 28 that provides power and timing signals to the radiation source 14 and a gantry motor controller 30 that controls the rotational speed and position of the gantry 12. A data acquisition system (DAS) 32 in the control mechanism 26 samples analog data from the detector elements 20 and converts the data to digital signals for subsequent processing. An image reconstructor 34 receives sampled and digitized radiation data from the DAS 32 and performs high-speed image reconstruction. The reconstructed image is applied as an input to a computer 36 that stores the image in a mass storage device 38.

The computer 36 also receives commands and scanning parameters from an operator via a console 40 that has, for example, a keyboard and/or other user input device(s). An associated display system 42 allows the operator to observe the reconstructed image and other data from the computer 36. The operator supplied commands and parameters are used by the computer 36 to provide control signals and information to the DAS 32, the radiation controller 28 and the gantry motor controller 30. In addition, the computer 36 operates a table motor controller 44 that controls a motorized table 46 to position the patient 22 in the gantry 12. In particular, the table 46 moves portions of the patient 22 through the gantry opening 48.

In one embodiment, the computer 36 includes a device 50, for example, a floppy disk drive, CD-ROM drive, or DVD-ROM drive, for reading instructions and/or data from a computer-readable medium 52, such as a floppy disk, CD-ROM, or DVD. It should be understood that other types of suitable computer-readable memory are recognized to exist (e.g., CD-RW and flash memory, to name just two), and that this description is not intended to exclude any of these. In another embodiment, the computer 36 executes instructions stored in firmware (not shown). Generally, a processor in at least one of the DAS 32, the reconstructor 34, and the computer 36 shown in FIG. 2 is programmed to execute the processes described below. Of course, the method is not limited to practice in CT imaging system 10 and can be utilized in connection with many other types and variations of imaging systems. In one embodiment, the computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
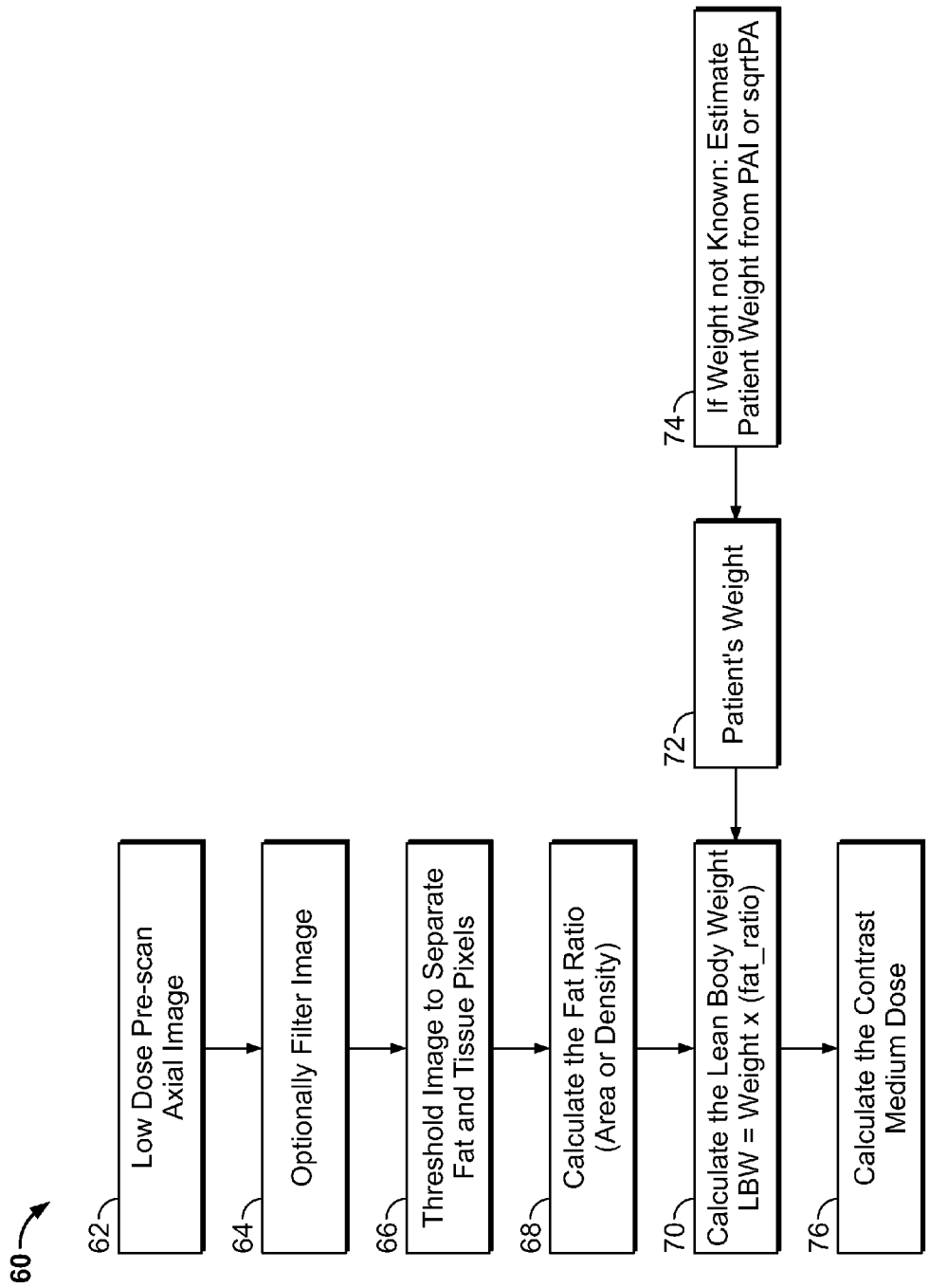
FIG. 3 is a flowchart illustrating a method for estimating Lean Body Weight (LBW) using CT data in accordance with various embodiments of the invention.

Various embodiments of the invention use CT information, which generally includes CT scan data, for example, CT image data, to estimate the body weight and/or fat content of an individual (e.g., a patient). In particular, a method 60 for estimating body weight and fat, for example, to estimate Lean Body Weight (LBW) using CT data is shown in FIG. 3. Specifically, at 62 CT image data is acquired, which in one embodiment is acquired from a low dose axial pre-scan to obtain a pre-scan axial image. For example, a low dose scout scan may be performed on an individual as is known, which may include injecting a patient with a lower dose of contrast agent and using a lower x-ray radiation power level, for example, ten times to twenty times lower x-ray radiation dose than a normal CT scan (e.g., a normal radiation level axial or helical scan).

In some embodiments, the scout scan acquires a single two-dimensional image of the individual being scanned with the CT imaging system. For example, during the scout scan the gantry of the CT imaging system may be rotated to a fixed position and the table translated into the bore of the gantry as x-ray radiation is projected. The scout scan may be limited to a target area or region of interest and based on the location of the individual within the gantry of the CT imaging system. When using the CT scout scan to acquire CT data to estimate the LBW, a narrow aperture may be used to perform the scan on, for example, the abdomen of the individual, which may include areas surrounding the abdomen or additional areas to allow for some deviations or variations in the CT imaging system. For example, in various embodiments, the CT scout scan is used to acquire CT data, such as a CT image, of the lower abdomen of an individual. However, different regions of the abdomen or the whole abdomen may be scanned.

The acquired low-dose scout scan image then may be optionally filtered at 64. The filtering may be performed on a currently acquired low-dose scout scan image or a previously acquired and stored low-dose scout scan image. The filtering may include, for example, a low pass filter of the low-dose scout scan image to reduce pixel variance, such as to reduce noise. Any known image filtering process or method may be used. In general, and for example, the filtering process may set a maximum noise level and a minimum noise level, and thereafter disregard pixels having a noise level above the maximum or below the minimum. As another example, the filtering process may reduce random noise by disregarding pixels having noise values than exceed a predetermined difference from an average or mean noise level of other pixels. Accordingly, some type of averaging or mean/standard deviation filtering may be performed.

A determination is then made at 66 as to which pixels in the CT data (e.g., CT image) acquired from the CT scout scan (which data may be raw data from a scan or filtered data at step 64) are pixels associated with or represent imaged fat (hereafter referred to as fat pixels) and which pixels are associated with or represent imaged tissue (hereafter referred to as tissue pixels). For example, a thresholding process may be performed to identify (and distinguish) fat pixels from tissue pixels. The thresholding process is essentially an image segmentation process wherein individual pixels of an image are identified and/or marked, for example, as fat pixels or tissue pixels. An adaptive thresholding process wherein different thresholds are used also may be provided, such as, to identify different type or kinds of fat or tissue. As another example, and in other various embodiments, dual energy CT (versus conventional CT) may be used wherein the linear attenuation coefficients of materials (i.e., HU values) are represented in a monochromatic CT image at a specific user selected keV (CT energy). Accordingly, the effective energy at which pixel values are determined is controlled rather than arbitrarily dependent on, for example, patient size, composition and energy distribution of detected x-ray photons. The range of pixel values for fat (as well as other tissues and materials) are more consistent and may be able to be more accurately identified for obtaining the lean body weight. Thus, the threshold values for fat may be indexed as a function of the keV in a monochromatic CT image created from a dual energy CT scan or energy discriminating CT detectors.

The thresholding values may be selected, for example, based on empirical studies, mathematical calculations, etc. In the various embodiments, the thresholding is set based on a typical or normal Hounsfield Unit (HU) range for fat and tissue pixels. The HU generally represent a pixel attenuation coefficient wherein water is assigned a value of zero and air is assigned a value of −1000. In various embodiments, a fat pixel threshold is set such the pixels having an HU value between about −150 HU and about −50 HU are identified as fat pixels and a tissue threshold is set such that pixels having an HU value greater than about −50 HU are identified as tissue pixels. However, it should be noted that these thresholding values may be changed or modified as desired or needed, for example, based on certain characteristics of an individual, a particular study, etc.

Accordingly, each pixel within the CT data acquired from the CT scout scan (or a portion or region of interest thereof) is identified as either a fat pixel or a tissue pixel. It should be noted that other thresholding values or ranges may be provided to identify different types or kinds of pixels other than fat pixels or tissue pixels (e.g., bone pixels), or sub-types of fat pixels or tissue pixels. Also, a thresholding process may be performed to identify and remove pixels corresponding to an imaged table on which an individual was imaged or is being imaged.

The identification of each of the pixels is stored. For example, a database or matrix of the identification may be stored, such that a pixel having a particular Cartesian or Polar coordinate has a pixel identifier (e.g., fat pixel identifier or tissue pixel identifier) associated therewith. Also, the fat pixel value (e.g., HU value) or the tissue pixel value (e.g., HU value) may also be stored in connection with each of the identified fat pixels and tissue pixels.

Once the pixels have been identified as either fat pixels or tissue pixels, a fat ratio is calculated at 68. The fat ratio may be a fat area ratio or a fat density ratio. In particular, a fat area ratio may be calculated by determining the ratio of the number of fat pixels to the total number of fat pixels plus tissue pixels as set forth in the following equation:

$$\text{total fat pixels}/(\text{total fat pixels}+\text{total tissue pixels}) \quad \text{Equation 1}$$

The fat density ratio may be calculated as the sum of the fat pixel values to the sum of the fat pixel values and the tissue pixel values as set forth in the following equation:

total fat pixel values/(total fat pixel values+total tissue pixel values)     Equation 2

Thereafter, a lean body weight (LBW) may be calculated at 70. In various embodiments, the LBW is calculated using the following equation:

(1−fat ratio)×weight of the imaged object(individual)     Equation 3

The LBW provides an estimate of the lean body weight corresponding to the object, for example, the individual imaged using the low dose pre-scan axial image. It should be noted that the weight of the imaged object may be determined at 72 based on weighing the object (individual) prior to the scout scan or based on a stored or previously recorded weight for the object. Alternatively, the weight of the imaged object may be estimated at 74 if the weight is not known at 72. In various embodiments, and for example, the weight of the imaged object may be estimated using Patient Attenuation Information (PAI) that is derived from the scout scan. The PAI may be determined, for example, as described in co-pending U.S. patent application Ser. No. 11/563,121 entitled "Methods and Apparatus for New Useful Metrics" commonly assigned. Once the PAI is determined, the weight of the imaged object may be estimated using the following equation:

Estimated Weight=11.995×PAI−161.62     Equation 4

In other various embodiments, the weight of the imaged object may be estimated using the square root of the projection area (sqrtPA) from the scout scan image. The sqrtPA may be determined, for example, as described in co-pending U.S. patent application Ser. No. 11/563,121 entitled "Methods and Apparatus for New Useful Metrics" commonly assigned. Once the sqrtPA is determined, the weight of the imaged object may be estimated using the following equation:

Estimated Weight=6.681×sqrtPA−161.63     Equation 5

It should be noted that the factors or values used in Equations 4 and 5 may be varied, for example, based on the scan parameters, scanning machine, etc.

Thereafter, a contrast medium dose optionally may be calculated at 76. For example, the contrast load for imaging an individual may be determined using a lookup table that is a function of the LBW. The lookup table may be generated using empirical data, mathematical calculation, etc. or as otherwise known. Thus, a more appropriate tailoring of pharmacologic intervention may be provided. For example, a dose and rate of contrast medium administration for abdominal multi-detector CT examinations may be determined as described in "*Determining Contrast Medium Dose and Rate on Basis of Lean Body Weight*", L. Ho, R. Nelson and D. Delong, Radiology, Volume 243: Number 2, May 2007.

Figure 4:
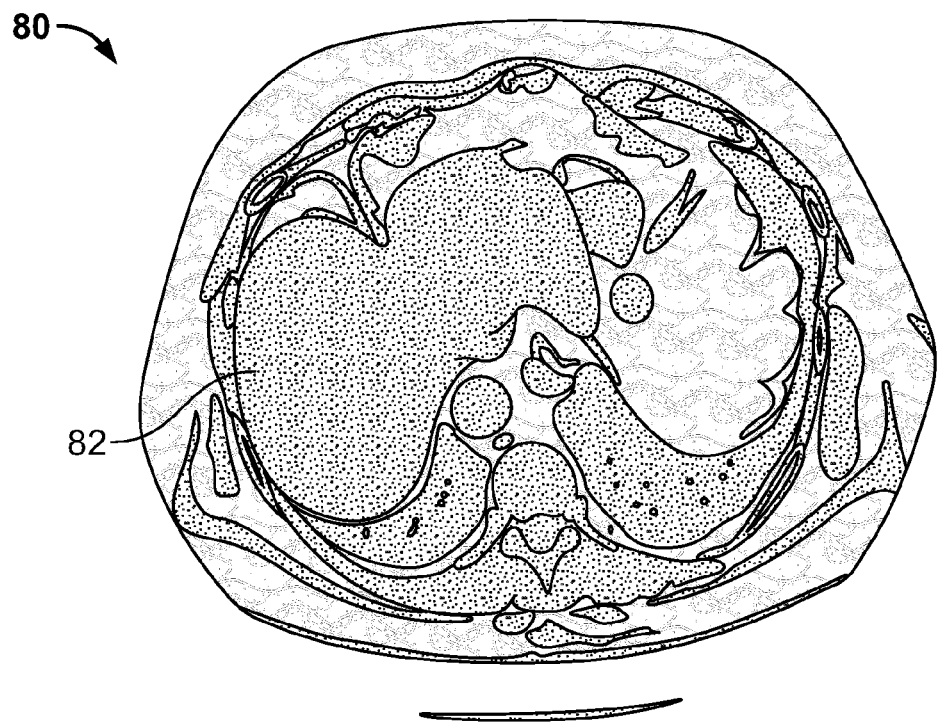
FIG. 4 is a CT image displaying only fat pixels in accordance with various embodiments of the invention.
Figure 5:
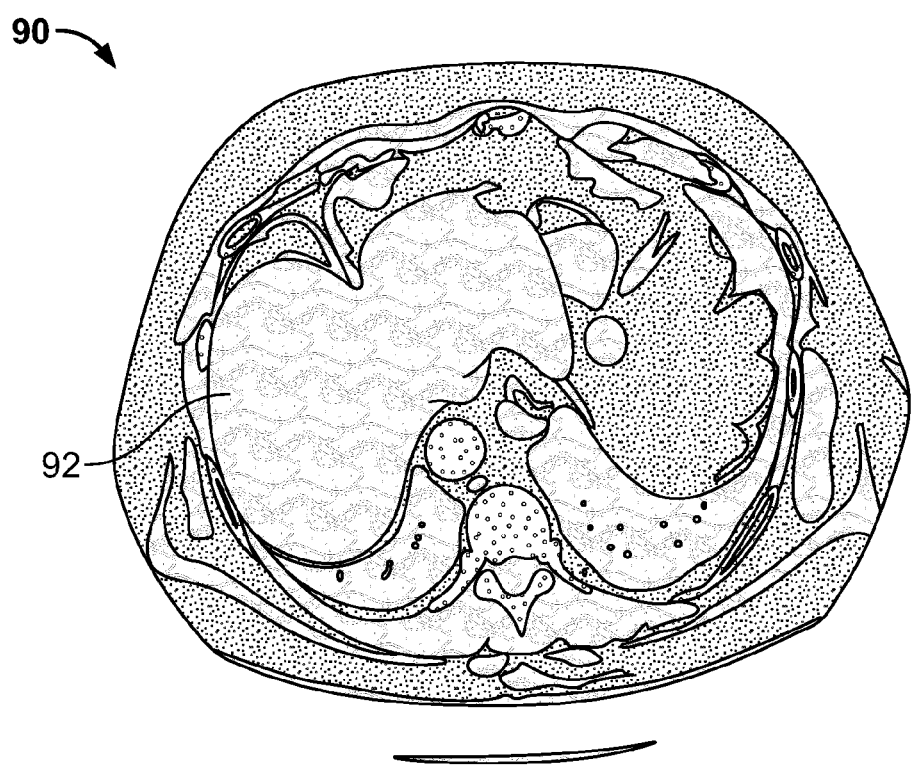
FIG. 5 is a CT image displaying only tissue pixels in accordance with various embodiments of the invention.

Once image data from a scout scan has been segmented or thresholded, for example, using the method 60 or a portion thereof, different images may be displayed, such as on the display system 42 (shown in FIG. 2). For example, once the fat pixels and tissue pixels have be identified, two different images may displayed, which may be displayed concurrently or separately on the same screen or on different screens. Exemplary images are shown in FIGS. 4 and 5 wherein the image 80 shown in FIG. 4 is a CT image displaying only fat pixels and the image 90 shown in FIG. 5 is a CT image displaying only tissue pixels. As can be seen, for example, in the fat pixel image 80, there is a pixel void 82 where pixels 92 of the liver as shown in FIG. 5 have been removed, for example, by the thresholding at 66 in the method 60 of FIG. 3. Thus, the tissue pixels of the liver have been removed in the image 80 that shows only fat pixels.

As an example, and referring to FIGS. 4 and 5, the method 60 when applied to the CT data used to generate the images 80 and 90, may result in the following exemplary values:

| | |
|---|---|
| Fat Area Ratio: | 0.37896 |
| Fat Density Ratio: | 0.34452 |
| PAI: | 33.2 |
| sqrtPA: | 59.1 |

Figure 6:
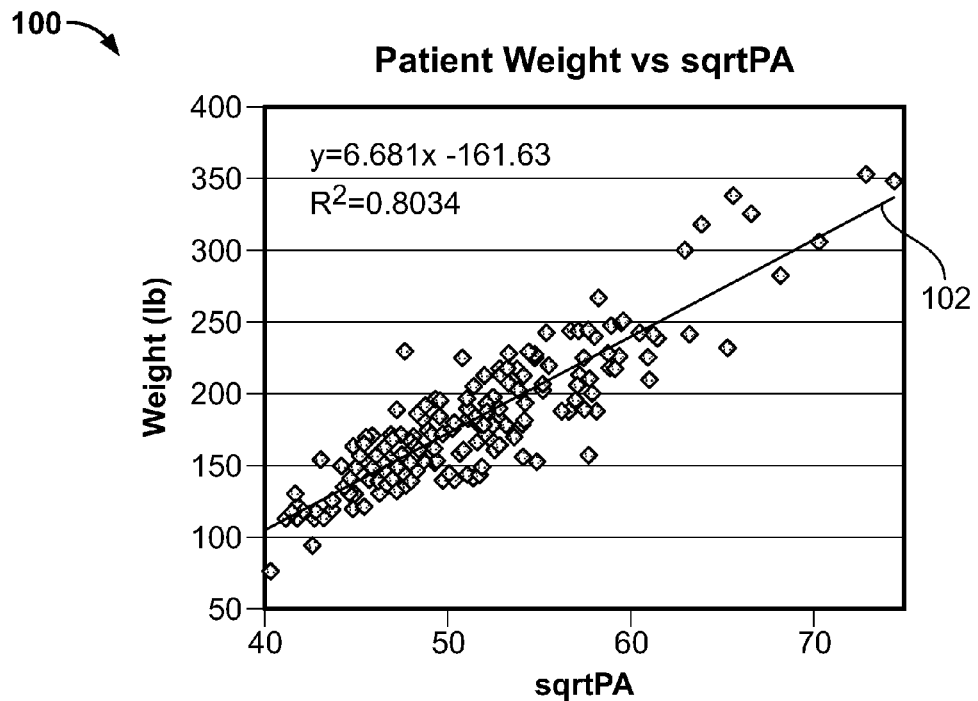
FIG. 6 is a graph illustrating that the square root of the projection area (sqrtPA) from a scout scan image correlates linearly with weight.
Figure 7:
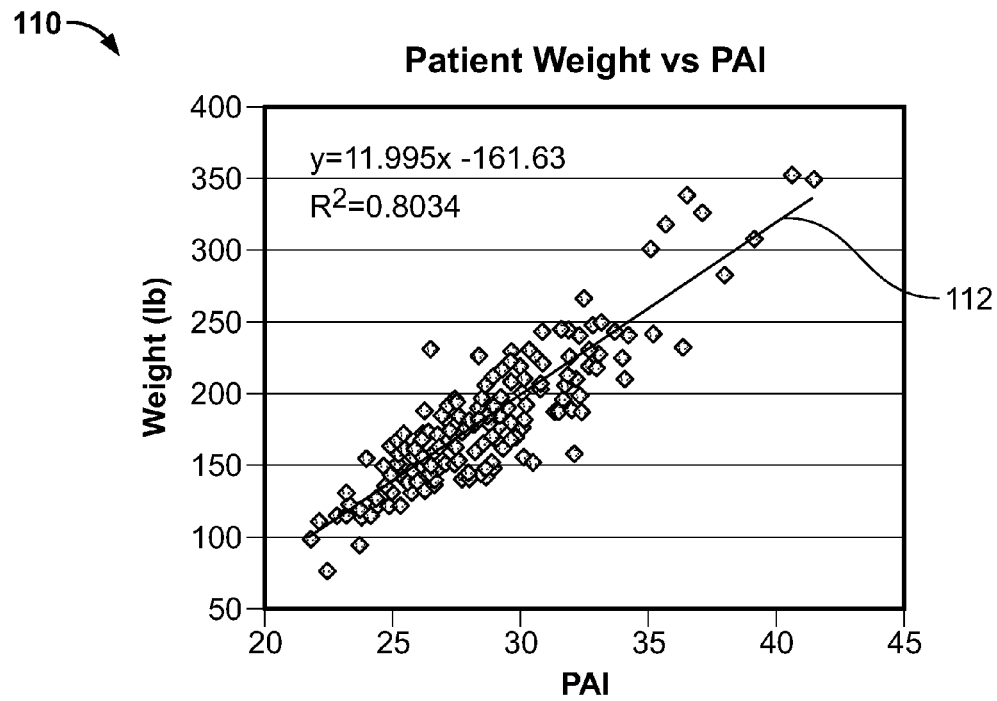
FIG. 7 is a graph illustrating that Patient Attenuation Information (PAI) from a scout scan correlates linearly with weight.

FIGS. 6 and 7 illustrate weight estimation coefficients. In particular, FIG. 6 is a graph 100 illustrating that the sqrtPA correlates linearly with weight as represented by the line 102 and FIG. 7 is a graph 110 illustrating that the PAI correlates linearly with weight as represented by the line 112.

Thus, various embodiments of the invention determine LBW using a CT scanner prior to a CT scan and without the use of, for example, a body composition weight analyzer. Using the LBW, a dose and rate of contrast medium administration can be determined.

The various embodiments or components, for example, the components of the CT imaging system of controllers or processors therein may be implemented as part of one or more computer systems, which may be separate from or integrated with other systems. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also store data or other information as desired or needed. The storage element may be in the form of an information source or a physical memory element within the processing machine.

The set of instructions may include various commands that instruct the computer as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining lean body weight, the method comprising:
   acquiring a pre-scan image using a computed tomography imaging system;
   segmenting the pre-scan image into pixels representing imaged fat and pixels representing imaged tissue; and
   determining a lean body weight based on the segmented pixels representing imaged fat and imaged tissue.

2. A method in accordance with claim 1 further comprising performing a scout scan to acquire the pre-scan image.

3. A method in accordance with claim 1 further comprising performing a low dose axial pre-scan to acquire the pre-scan image.

4. A method in accordance with claim 1 wherein the segmenting comprises thresholding the pre-scan image to segment the pre-scan image into pixels representing imaged fat and pixels representing imaged tissue.

5. A method in accordance with claim 4 wherein the thresholding comprises setting a different threshold range for pixels representing imaged fat and pixels representing imaged tissue.

6. A method in accordance with claim 5 wherein a threshold range for pixels representing imaged fat is between about −150 Hounsfield Units (HU) and about −50 HU.

7. A method in accordance with claim 5 wherein a threshold range for pixels representing image tissue is greater than about −50 Hounsfield Units (HU).

8. A method in accordance with claim 4 wherein the thresholding comprises indexing at least one threshold value for pixels representing imaged fat as a function of a keV in a monochromatic computed tomography image formed from one of a dual energy computed tomography scan and energy discriminating computed tomography detectors.

9. A method in accordance with claim 1 further comprising calculating a fat area ratio to determine the lean body weight.

10. A method in accordance with claim 9 wherein calculating the fat area ratio comprises calculating a ratio of (i) a number of pixels representing imaged fat to (ii) a total number of pixels representing imaged fat plus a total number of pixels representing imaged tissue.

11. A method in accordance with claim 10 wherein determining the lean body weight comprises multiplying a weight of an object represented at least in part by the pre-scan image with (1−the fat area ratio).

12. A method in accordance with claim 1 further comprising calculating a fat density ratio to determine the lean body weight.

13. A method in accordance with claim 12 wherein calculating the fat density ratio comprises calculating a ratio of (i) a sum of values of pixels representing imaged fat to (ii) a sum of values of pixels representing imaged fat and imaged tissue.

14. A method in accordance with claim 13 wherein determining the lean body weight comprises multiplying a weight of an object represented at least in part by the pre-scan image with (1−the fat density ratio).

15. A method in accordance with claim 1 further comprising filtering the pre-scan image.

16. A method in accordance with claim 1 further comprising calculating a contrast medium dose based on the determined lean body weight.

17. A method in accordance with claim 1 further comprising performing a scout scan of an abdomen of a person to acquire the pre-scan image.

18. A method in accordance with claim 1 further comprising performing a scout scan of a lower abdomen of a person to acquire the pre-scan image.

19. A method for determining lean body weight of a person using a computed tomography (CT) scan, the method comprising:
   performing a scout scan of an abdomen of the person to acquire an image;
   thresholding the image to identify pixels representing imaged fat and pixels representing imaged tissue;
   calculating a fat ratio based on the identified pixels representing imaged fat and imaged tissue; and
   determining a lean body weight for the person based on the fat ratio and a weight of the person.

20. A method in accordance with claim 19 wherein the weight of the person comprises a measured weight of the person.

21. A method in accordance with claim 19 wherein the weight of the person comprises an estimated weight of the person using one of a Patient Attenuation Information (PAI) from the scout scan and a square root of the projection area (sqrtPA) from the scout scan.

22. A method in accordance with claim 19 further comprising identifying and removing pixels representing a table on which the person is imaged.

23. A computed tomography system comprising:
   an imaging portion configured to acquire a scout scan of a person; and
   a processing portion configured to threshold an image generated from the scout scan to identify pixels representing imaged fat and pixels representing imaged tissue, and to calculate a lean body weight of the person based on a fat ratio determined from the identified pixels.

* * * * *